(12) United States Patent
Motoi et al.

(10) Patent No.: US 9,975,843 B2
(45) Date of Patent: May 22, 2018

(54) BIFUNCTIONAL COMPOUND HAVING NORBORNANE SKELETON AND METHOD FOR PRODUCING SAME

(71) Applicant: MITSUBISHI GAS CHEMICAL COMPANY, INC., Chiyoda-ku (JP)

(72) Inventors: Takashi Motoi, Okayama (JP); Mitsuharu Kitamura, Niigata (JP); Manabu Hirakawa, Tokyo (JP)

(73) Assignee: MITSUBISHI GAS CHEMICAL COMPANY, INC., Chiyoda-ku (JP)

( * ) Notice: Subject to any disclaimer, the term of this patent is extended or adjusted under 35 U.S.C. 154(b) by 0 days. days.

(21) Appl. No.: 15/127,969

(22) PCT Filed: Mar. 27, 2015

(86) PCT No.: PCT/JP2015/059554
§ 371 (c)(1),
(2) Date: Sep. 21, 2016

(87) PCT Pub. No.: WO2015/147242
PCT Pub. Date: Oct. 1, 2015

(65) Prior Publication Data
US 2017/0088504 A1    Mar. 30, 2017

(30) Foreign Application Priority Data

Mar. 28, 2014  (JP) ................... 2014-068472
Mar. 28, 2014  (JP) ................... 2014-068473

(51) Int. Cl.
| | | |
|---|---|---|
| C07C 67/36 | (2006.01) |
| C07C 69/757 | (2006.01) |
| C07C 29/141 | (2006.01) |
| C07C 29/149 | (2006.01) |
| C07C 67/347 | (2006.01) |
| C07C 45/50 | (2006.01) |
| C07C 47/347 | (2006.01) |
| C08G 64/02 | (2006.01) |

(52) U.S. Cl.
CPC .......... *C07C 69/757* (2013.01); *C07C 29/141* (2013.01); *C07C 29/149* (2013.01); *C07C 45/50* (2013.01); *C07C 47/347* (2013.01); *C07C 67/347* (2013.01); *C08G 64/0208* (2013.01); *C07C 2603/86* (2017.05)

(58) Field of Classification Search
None
See application file for complete search history.

(56) References Cited

U.S. PATENT DOCUMENTS

2009/0156856 A1    6/2009 Ohara et al.

FOREIGN PATENT DOCUMENTS

| GB | 1170226 | 11/1969 |
|---|---|---|
| JP | 5-125329 A | 5/1993 |
| JP | 5-155964 A | 6/1993 |
| JP | 11-80067 A | 3/1999 |
| JP | 11-80068 A | 3/1999 |
| JP | 11-100339 A | 4/1999 |
| JP | 2001-10999 A | 1/2001 |
| JP | 2001-11008 A | 1/2001 |
| JP | 2007-161917 A | 6/2007 |
| JP | 2009227614 A | * 10/2009 |
| WO | 2007/032385 A1 | 3/2007 |

OTHER PUBLICATIONS

International Search Report dated Jun. 23, 2015 in PCT/JP2015/059554 filed Mar. 27, 2015.

* cited by examiner

*Primary Examiner* — Sudhakar Katakam
*Assistant Examiner* — Ana Z Muresan
(74) *Attorney, Agent, or Firm* — Oblon, McClelland, Maier & Neustadt, L.L.P.

(57) ABSTRACT

A method for producing a bifunctional compound of formula (1):

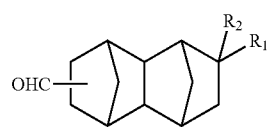

where $R_1$ represents $COOCH_3$, $COOC_2H_5$, $COOC_3H_7$, $COOC_4H_9$ or CHO and $R_2$ represents H, $CH_3$ or $C_2H_5$, by subjecting a monoolefin of formula (2):

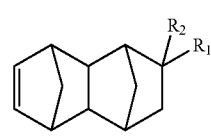

where $R_1$ represents $COOCH_3$, $COOC_2H_5$, $COOC_3H_7$, $COOC_4H_9$ or CHO and $R_2$ represents H, $CH_3$ or $C_2H_5$, carbon monoxide and hydrogen gases to a hydroformylation reaction in the presence of a rhodium compound and an organic phosphorous compound. Compounds produced.

11 Claims, 6 Drawing Sheets

[Figure 1]
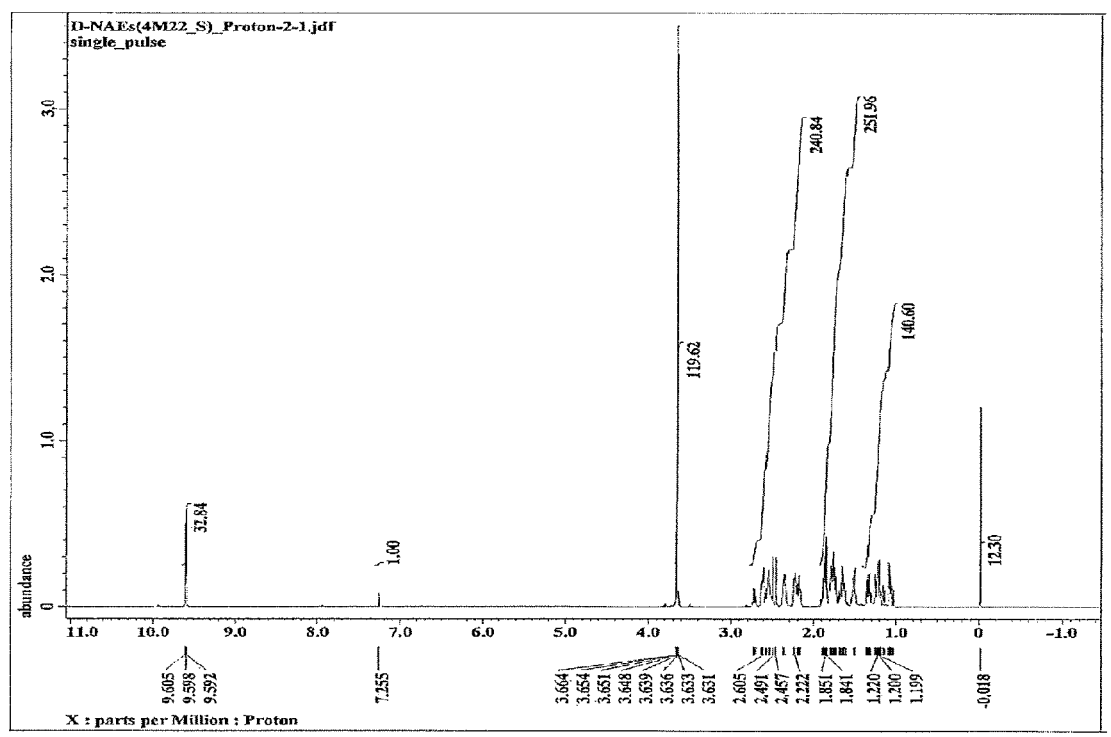

[Figure 2]
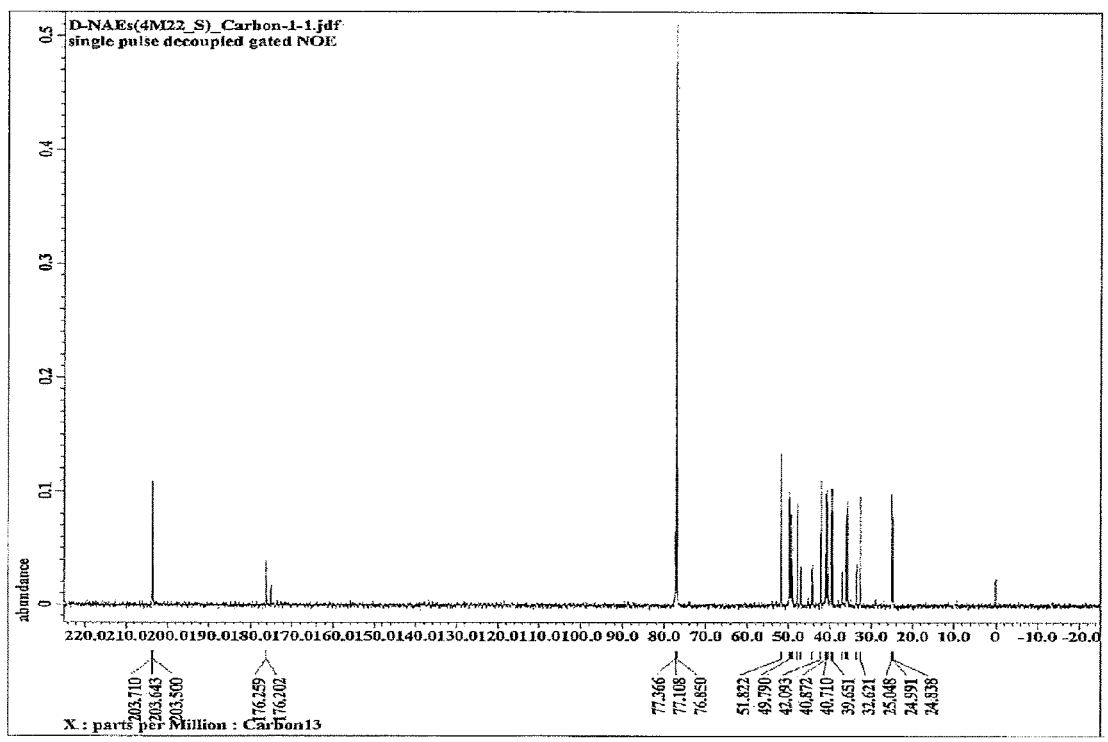

[Figure 3]
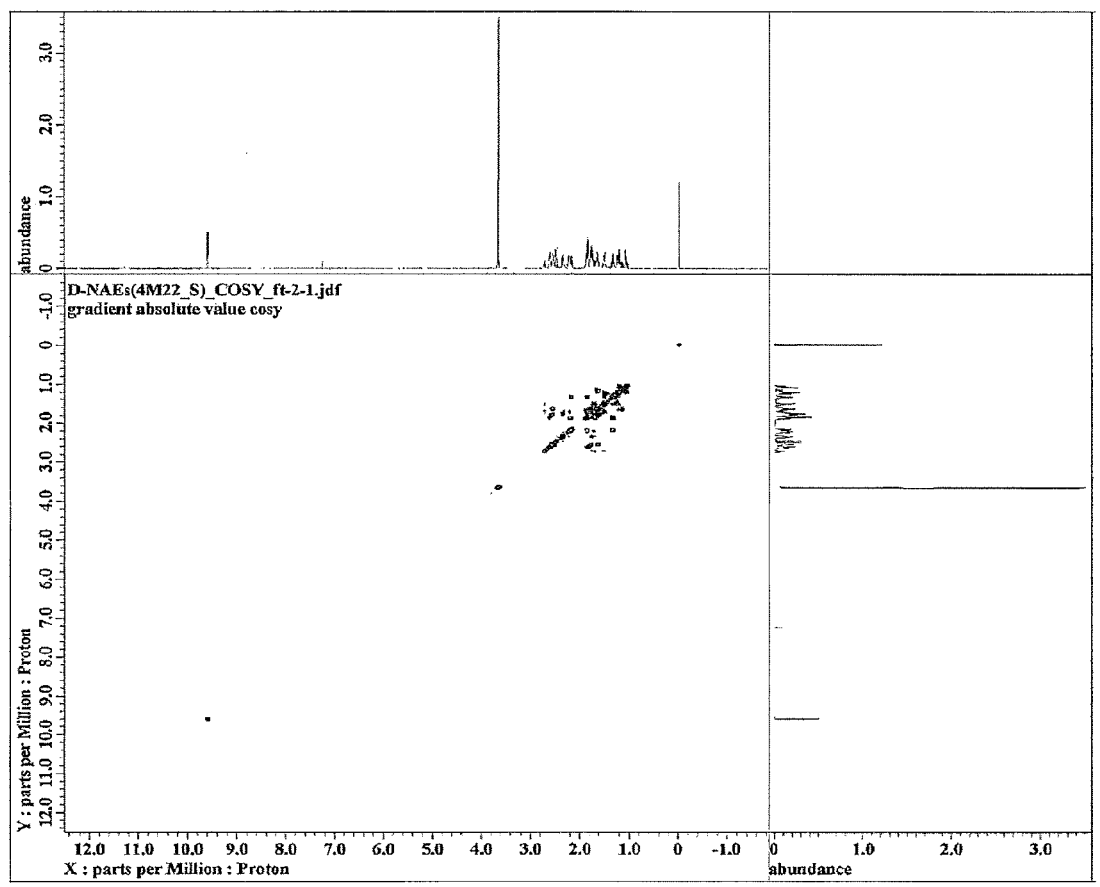

[Figure 4]
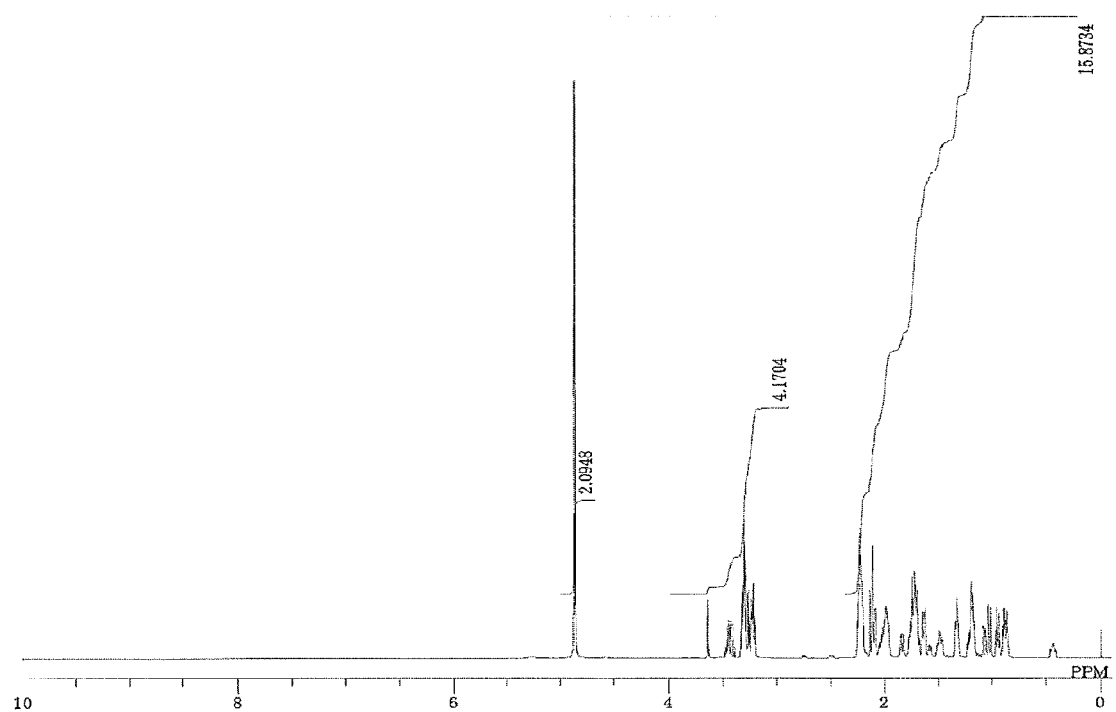

[Figure 5]
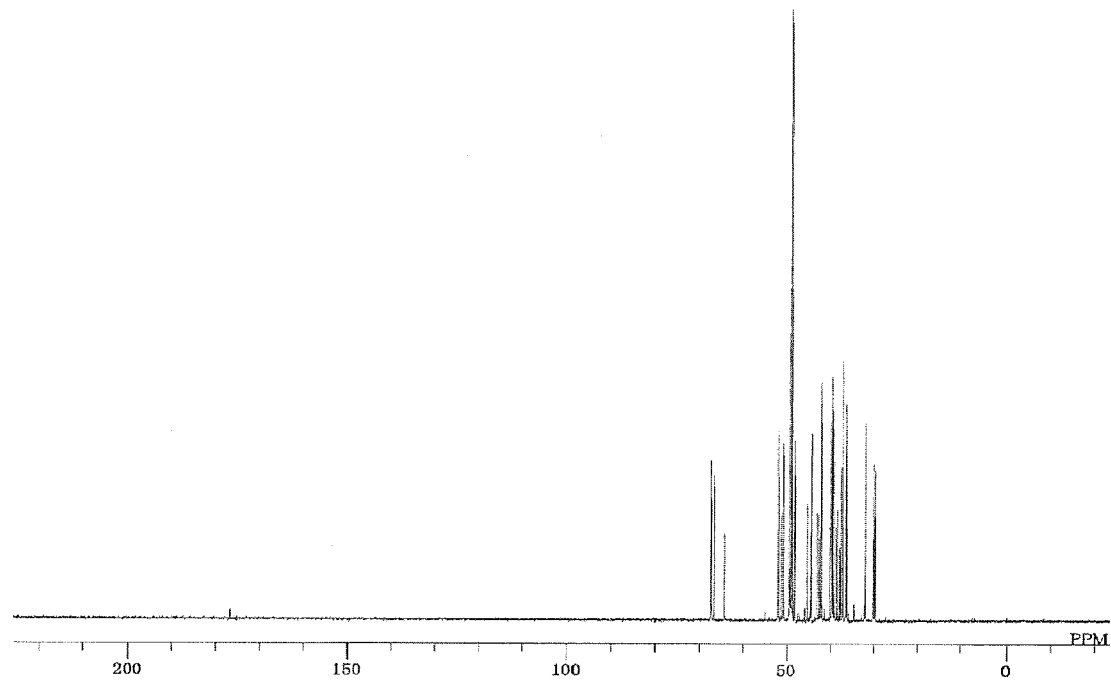

[Figure 6]
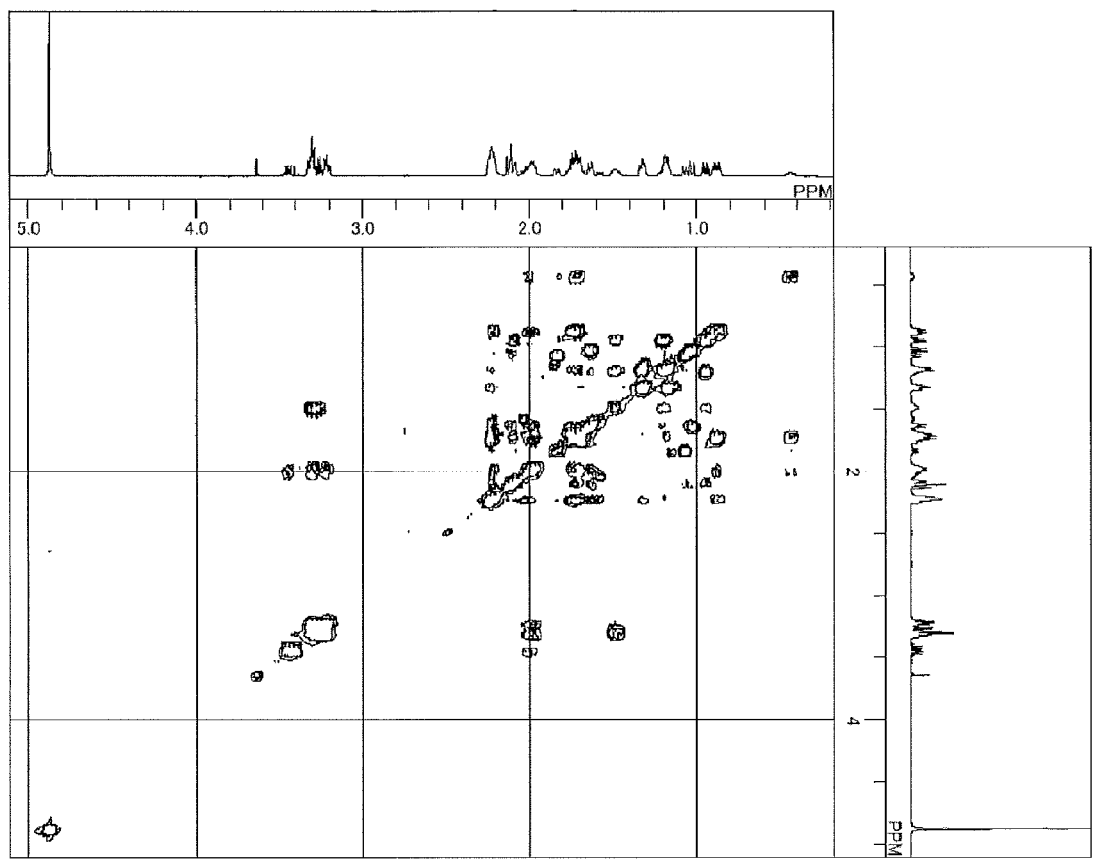

BIFUNCTIONAL COMPOUND HAVING NORBORNANE SKELETON AND METHOD FOR PRODUCING SAME

TECHNICAL FIELD

The present invention relates to a bifunctional compound useful as a paint additive, adhesive, resin raw material or the like and a method for producing the same, and particularly relates to a bifunctional compound having a norbornane skeleton in the molecule and a method for producing the same.

BACKGROUND ART

It is known that a bifunctional compound having a norbornane skeleton exhibits excellent characteristics when used as an adhesive or resin raw material. As the bifunctional compound having a norbornane skeleton, tricyclodecane dicarbaldehyde and pentacyclopentadecane dicarbaldehyde are known, and several production methods have been reported (Patent Document 1).

Patent Documents 2 to 4 describe that tricyclodecane dicarbaldehyde is obtained by hydroformylating dicyclopentadiene in the presence of a rhodium catalyst using a mixed gas of carbon monoxide and hydrogen. Further, Patent Document 5 describes that tricyclodecane dicarbaldehyde or pentacyclopentadecane dicarbaldehyde is obtained by hydroformylating dicyclopentadiene or tricyclopentadiene in the presence of a rhodium catalyst using a mixed gas of carbon monoxide and hydrogen.

The tricyclodecane dicarbaldehyde described in Patent Documents 2 to 5 is a compound in which one norbornane and cyclopentane share a plurality of atoms with each other to form the main skeleton as shown in formula (5) below. Further, the pentacyclopentadecane dicarbaldehyde described in Patent Document 5 is a compound in which two norbornanes and cyclopentane share a plurality of atoms with each other to form the main skeleton as shown in formula (6) or (7) below.

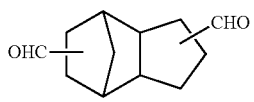
(5)

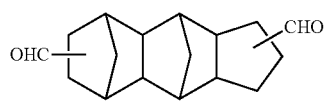
(6)

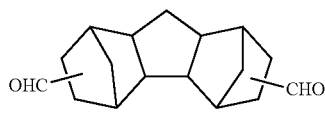
(7)

In Patent Document 2, tricyclodecane dicarbaldehyde is produced by hydroformylating dicyclopentadiene under a high-pressure condition of about 20 to 25 MPa. Accordingly, equipments having high pressure resistance are required in industrial practice, and therefore it is hardly a method excellent in economic efficiency.

Patent Documents 3 and 4 relate to a method for the production of tricyclodecane dicarbaldehyde, and it is characterized in that tricyclodecane dicarbaldehyde is produced by hydroformylating dicyclopentadiene using a slight amount of a rhodium catalyst by controlling the concentration of conjugated diene which is a catalyst poison. However, also in these patent documents, a reaction pressure of at least 9 MPa is required in order to achieve a high yield, and therefore it is desired to develop a method for obtaining a bifunctional compound by means of a reaction under lower pressure condition.

Patent Document 5 relates to a method for the production of tricyclodecane dicarbaldehyde or pentacyclopentadecane dicarbaldehyde, wherein: dicyclopentadiene or tricyclopentadiene is hydroformylated using a rhodium compound as a catalyst; an extraction solvent made of a polyhydric alcohol is added to the obtained reaction solution; tricyclodecane dicarbaldehyde or pentacyclopentadecane dicarbaldehyde that is the reaction product is separated into an extraction solvent layer; and a rhodium complex catalyst is separated into a hydrocarbon-based reaction solvent layer. In order to reduce the cost for the catalyst, it is required to circulate and recycle the rhodium complex catalyst, and equipments for that is essential. Therefore, it is hardly an economical method.

Patent Document 2 also describes a method for producing tricyclodecane dimethanol by hydroformylating dicyclopentadiene to provide dialdehyde and subsequent hydrogenation of this dialdehyde.

Patent Document 6 describes a method for producing tricyclodecane dimethanol, wherein: dicyclopentadiene is subjected to a hydroformylation reaction using a catalyst made of rhodium-phosphite in the presence of a solvent and a tertiary amine compound; and the hydroformylation reaction solution is subjected to hydrogen reduction in the presence of a hydrogenation catalyst.

Patent Document 7 describes a method for producing tricyclodecane dimethanol or pentacyclopentadecane dimethanol, wherein: dicyclopentadiene or tricyclopentadiene is hydroformylated using a rhodium compound as a catalyst; an extraction solvent made of a polyhydric alcohol is added to the obtained reaction solution; a rhodium complex catalyst is separated into a hydrocarbon-based reaction solvent layer; tricyclodecane dicarbaldehyde or pentacyclopentadecane dicarbaldehyde that is the reaction product is separated into an extraction solvent layer; and after that, the extraction solvent layer is subjected to hydrogen reduction in the presence of a hydrogenation catalyst.

The tricyclodecane dimethanol described in Patent Documents 2, 6 and 7 is a compound in which one norbornane and cyclopentane share a plurality of atoms with each other to form the main skeleton as shown in formula (8) below. Further, the pentacyclopentadecane dimethanol described in Patent Document 7 is a compound in which two norbornanes and cyclopentane share a plurality of atoms with each other to form the main skeleton as shown in formula (9) or (10) below.

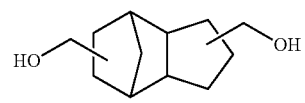
(8)

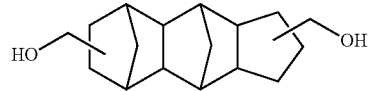
(9)

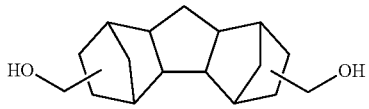

Patent Document 2 relates to a method for producing tricyclodecane dimethanol in which a high-pressure condition of about 20 to 25 MPa is required. Accordingly, equipments having high pressure resistance are required in industrial practice, and therefore it is hardly a method excellent in economic efficiency.

Regarding the method for producing tricyclodecane dimethanol described in Patent Document 6, in order to achieve a high yield in dialdehyde synthesis based on the hydroformylation reaction, a reaction pressure of at least 9 MPa is required, and therefore it is desired to develop a method for obtaining a bifunctional compound by means of a reaction under lower pressure. Further, when the hydroformylation reaction is performed with a concentration of the rhodium catalyst by which the reaction proceeds and then hydrogen reduction is carried out in the presence of a hydrogenation catalyst, a rhodium complex that is a hydroformylation catalyst is reduced, while the hydrogenation catalyst is poisoned by phosphite contained in the hydroformylation reaction solution, resulting in the problem of increase in the cost for the catalyst.

In the method for producing tricyclodecane dimethanol or pentacyclopentadecane dimethanol described in Patent Document 7, in order to reduce the cost for the rhodium catalyst, it is required to recycle the hydrocarbon-based reaction solvent layer containing the rhodium complex catalyst, and equipments for that is required. Therefore, it is hardly an economical method.

Patent Document 8 describes a bifunctional compound having a tetracyclododecane skeleton, but does not describe any method for producing the bifunctional compound. In addition, Patent Document 8 discloses intended use of polyester resin, but only describes cases of using a 2,6-derivative of the bifunctional compound or a 2,7-derivative of the bifunctional compound independently, and the largest amount of the bifunctional compound used is just 5 mol %. Further, the document does not describe intended use of polycarbonate resin.

PRIOR ART DOCUMENTS

Patent Documents

Patent Document 1: Japanese Laid-Open Patent Publication No. H05-125329
Patent Document 2: GB Patent No. 1170226
Patent Document 3: Japanese Laid-Open Patent Publication No. H11-80067
Patent Document 4: Japanese Laid-Open Patent Publication No. H11-80068
Patent Document 5: Japanese Laid-Open Patent Publication No. 2001-11008
Patent Document 6: Japanese Laid-Open Patent Publication No. H11-100339
Patent Document 7: Japanese Laid-Open Patent Publication No. 2001-10999
Patent Document 8: Japanese Laid-Open Patent Publication No. 2007-161917

SUMMARY OF THE INVENTION

Problems to be Solved by the Invention

Examples of intended uses of bifunctional compounds include a paint additive, an adhesive and a resin raw material. It is generally known that characteristics of a paint, an adhesive, a resin, etc. can be modified by using a bifunctional compound having a different molecular structure in these intended uses. For this reason, a novel bifunctional compound is desired in terms of modification, improvement of characteristics, imparting function, etc. Specifically, the purpose of the present invention is to provide a novel bifunctional compound having a norbornane skeleton in the molecule and having a skeleton different from those of tricyclodecane dicarbaldehyde and pentacyclopentadecane dicarbaldehyde. Another purpose of the present invention is to provide an isomer mixture comprising novel bifunctional compounds having a norbornane skeleton in the molecule and having a skeleton different from those of tricyclodecane dimethanol and pentacyclopentadecane dimethanol.

Yet another purpose of the present invention is to provide a production method, which is industrially practicable and excellent in economic efficiency, for providing a novel bifunctional compound having a norbornane skeleton in the molecule.

Means for Solving the Problems

The present inventors diligently made researches in order to solve the above-described problems, and found that the problems can be solved by the present invention described below.

Specifically, the present invention is as follows:

<1> A bifunctional compound represented by formula (1) below:

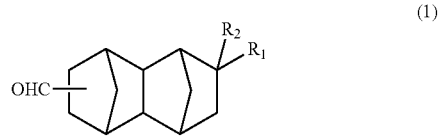

wherein: $R_1$ represents $COOCH_3$, $COOC_2H_5$, $COOC_3H_7$, $COOC_4H_9$ or CHO; and $R_2$ represents H, $CH_3$ or $C_2H_5$.

<2> A method for producing a bifunctional compound represented by formula (1) below:

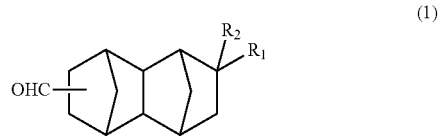

wherein: $R_1$ represents $COOCH_3$, $COOC_2H_5$, $COOC_3H_7$, $COOC_4H_9$ or CHO; and $R_2$ represents H, $CH_3$ or $C_2H_5$, the method having a step of subjecting a monoolefin represented by formula (2) below:

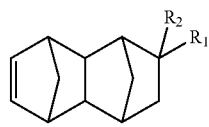

(2)

wherein: $R_1$ represents $COOCH_3$, $COOC_2H_5$, $COOC_3H_7$, $COOC_4H_9$ or CHO; and $R_2$ represents H, $CH_3$ or $C_2H_5$, carbon monoxide and hydrogen gases to a hydroformylation reaction in the presence of a rhodium compound and an organic phosphorous compound.

<3> The method according to item <2>, which has a step of producing the monoolefin represented by formula (2) by a Diels-Alder reaction of $CH_2\!=\!CR_1R_2$ (in the formula: $R_1$ represents $COOCH_3$, $COOC_2H_5$, $COOC_3H_7$, $COOC_4H_9$ or CHO; and $R_2$ represents H, $CH_3$ or $C_2H_5$) with dicyclopentadiene.

<4> The method according to item <2> or <3>, wherein the hydroformylation reaction is performed using: the rhodium compound in an amount of 0.1 to 60 μmol relative to 1 mol of the monoolefin represented by formula (2); and the organic phosphorous compound in an amount of 300 to 10000 times the molar quantity of the rhodium compound.

<5> The method according to any one of items <2> to <4>, wherein the pressure at the time of hydroformylation of the monoolefin represented by formula (2) is 1 to 12 MPa.

<6> The method according to any one of items <2> to <5>, wherein the monoolefin represented by formula (2) or a solution thereof is supplied to a solution comprising the rhodium compound, the organic phosphorous compound and a solvent under an atmosphere comprising carbon monoxide and hydrogen gases.

<7> The method according to any one of items <2> to <6>, wherein the bifunctional compound represented by formula (1) is isolated from a reaction solution after the hydroformylation reaction by means of distillation.

<8> A method for producing a bifunctional compound represented by formula (3) below:

(3)

wherein $R_2$ represents H, $CH_3$ or $C_2H_5$, the method having a step of reducing a bifunctional compound represented by formula (1) below:

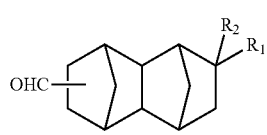

(1)

wherein: $R_1$ represents $COOCH_3$, $COOC_2H_5$, $COOC_3H_7$, $COOC_4H_9$ or CHO; and $R_2$ represents H, $CH_3$ or $C_2H_5$, in the presence of a catalyst having hydrogenation activity and hydrogen.

<9> The method according to item <8>, wherein the catalyst having hydrogenation activity comprises at least one element selected from the group consisting of copper, chromium, iron, zinc, aluminium, nickel, cobalt and palladium.

<10> The method according to item <8> or <9>, which has a step of producing the bifunctional compound represented by formula (1) by subjecting a monoolefin represented by formula (2) below:

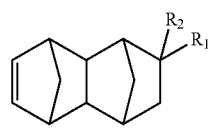

(2)

wherein: $R_1$ represents $COOCH_3$, $COOC_2H_5$, $COOC_3H_7$, $COOC_4H_9$ or CHO; and $R_2$ represents H, $CH_3$ or $C_2H_5$, carbon monoxide and hydrogen gases to a hydroformylation reaction in the presence of a rhodium compound and an organic phosphorous compound.

<11> The method according to item <10>, wherein the hydroformylation reaction is performed using: the rhodium compound in an amount of 0.1 to 60 μmol relative to 1 mol of the monoolefin represented by formula (2); and the organic phosphorous compound in an amount of 300 to 10000 times the molar quantity of the rhodium compound.

<12> An isomer mixture of: a 2,6-derivative of a bifunctional compound represented by formula (3-a) below:

(3-a)

wherein $R_2$ represents H, $CH_3$ or $C_2H_5$; and a 2,7-derivative of a bifunctional compound represented by formula (3-b) below:

(3-b)

wherein $R_2$ represents H, $CH_3$ or $C_2H_5$, wherein the mixing ratio between the 2,6-derivative and the 2,7-derivative is 20:80 to 80:20.

Advantageous Effect of the Invention

According to the present invention, it is possible to obtain a novel bifunctional compound having a norbornane skeleton in the molecule by means of a method which is industrially practicable and excellent in economic efficiency.

BRIEF DESCRIPTION OF THE DRAWINGS

FIG. 1 shows results of the 1H-NMR measurement of the main reaction product obtained in Example 1A.
FIG. 2 shows results of the 13C-NMR measurement of the main reaction product obtained in Example 1A.
FIG. 3 shows results of the COSY-NMR measurement of the main reaction product obtained in Example 1A.

FIG. 4 shows results of the 1H-NMR measurement of the main reaction product obtained in Example 1B.

FIG. 5 shows results of the 13C-NMR measurement of the main reaction product obtained in Example 1B.

FIG. 6 shows results of the COSY-NMR measurement of the main reaction product obtained in Example 1B.

EMBODIMENTS FOR CARRYING OUT THE INVENTION

Hereinafter, the mode for carrying out the present invention (hereinafter just referred to as "the present embodiment") will be described in detail. The present embodiment described below is provided for illustrative purposes, and it is not intended that the present invention be limited only to the content described below. The present invention can be suitably modified and then practiced within the gist of the present invention.

The bifunctional compound of the present embodiment is a compound represented by formula (1) below:

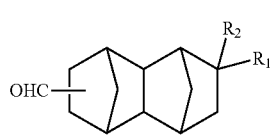

(1)

In the formula, $R_1$ represents $COOCH_3$, $COOC_2H_5$, $COOC_3H_7$, $COOC_4H_9$ or CHO, and $R_2$ represents H, $CH_3$ or $C_2H_5$. $R_1$ is preferably $COOCH_3$ or CHO, and $R_2$ is preferably H or $CH_3$. Further, an embodiment in which $R_1$ represents CHO while $R_2$ represents $C_2H_5$ is also preferred.

Such a bifunctional compound having a norbornane skeleton represented by formula (1) exhibits excellent characteristics when used as an adhesive or resin raw material.

The bifunctional compound represented by formula (1) of the present embodiment can be produced by subjecting a $C_{13-19}$ monoolefin represented by formula (2) below, carbon monoxide and hydrogen gases to a hydroformylation reaction in the presence of a rhodium compound and an organic phosphorous compound.

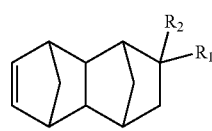

(2)

In the formula, $R_1$ represents $COOCH_3$, $COOC_2H_5$, $COOC_3H_7$, $COOC_4H_9$ or CHO, and $R_2$ represents H, $CH_3$ or $C_2H_5$. $R_1$ is preferably $COOCH_3$ or CHO, and $R_2$ is preferably H or $CH_3$. Further, an embodiment in which $R_1$ represents CHO while $R_2$ represents $C_2H_5$ is also preferred.

In the present embodiment, the $C_{13-19}$ monoolefin represented by formula (2) can be produced by performing a Diels-Alder reaction of a monoolefin having a functional group with dicyclopentadiene.

Examples of the olefin having a functional group to be used for the Diels-Alder reaction include methyl methacrylate, ethyl methacrylate, propyl methacrylate, butyl methacrylate, methyl acrylate, ethyl acrylate, propyl acrylate, butyl acrylate, methacrolein and acrolein. More preferred examples of the olefin include methyl methacrylate, ethyl methacrylate, methyl acrylate, ethyl acrylate, methacrolein, acrolein and ethylacrolein.

The dicyclopentadiene to be used for the Diels-Alder reaction in the present embodiment preferably has a high purity, and it is desirable that inclusion of butadiene, isoprene, etc. is avoided as much as possible. The purity of the dicyclopentadiene is more preferably 90% or more, and even more preferably 95% or more. Further, since it is known that dicyclopentadiene is depolymerized under heating conditions to obtain cyclopentadiene (so-called "monocyclopentadiene"), it is also possible to use cyclopentadiene instead of dicyclopentadiene. Note that it is considered that the $C_{13-19}$ monoolefin represented by formula (2) is substantially produced via a $C_{8-14}$ monoolefin represented by formula (4) below (first-step Diels-Alder reaction product), and that the produced monoolefin represented by formula (4), as a new dienophile, and cyclopentadiene, as a diene, existing in the reaction system are reacted in the Diels-Alder reaction (second-step Diels-Alder reaction) to produce the $C_{13-19}$ monoolefin represented by formula (2).

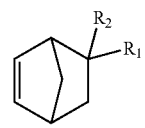

(4)

In the formula, $R_1$ represents $COOCH_3$, $COOC_2H_5$, $COOC_3H_7$, $COOC_4H_9$ or CHO, and $R_2$ represents H, $CH_3$ or $C_2H_5$. $R_1$ is preferably $COOCH_3$ or CHO, and $R_2$ is preferably H or $CH_3$. Further, an embodiment in which $R_1$ represents CHO while $R_2$ represents $C_2H_5$ is also preferred.

For efficient progress of the 2-step Diels-Alder reaction described above, existence of cyclopentadiene in the reaction system is important. For this reason, the reaction temperature is preferably 100° C. or higher, more preferably 120° C. or higher, and particularly preferably 130° C. or higher. Meanwhile, for suppressing by-production of a high-boiling-point substance, the reaction is preferably performed at 250° C. or lower. Further, as a reaction solvent, hydrocarbons, alcohols, esters, etc. can be used, and preferred are aliphatic hydrocarbons having 6 or more carbon atoms, cyclohexane, toluene, xylene, ethylbenzene, mesitylene, propanol, butanol, etc.

As the reaction method of the Diels-Alder reaction of the present embodiment, various reaction methods can be employed, and examples thereof include: the batch method using a tank reactor or the like; the semibatch method in which a substrate or substrate solution is supplied to a tank reactor under reaction conditions; and the continuous flow method in which substrates are flowed through a tube reactor under reaction conditions.

The reaction product obtained by the Diels-Alder reaction of the present embodiment can be directly used as a raw material for the next hydroformylation reaction, but may also be purified by means of distillation, extraction, crystallization or the like and then used in the next process.

The bifunctional compound represented by formula (1) of the present embodiment can be produced by subjecting the monoolefin represented by formula (2), carbon monoxide and hydrogen gases to a hydroformylation reaction in the presence of a rhodium compound and an organic phosphorous compound, and if required, a solvent.

Regarding the rhodium compound to be used for the hydroformylation reaction in the present embodiment, the form of a precursor thereof is not limited as long as the rhodium compound is a compound which forms a complex together with the organic phosphorous compound and exhibits hydroformylation activity in the presence of carbon monoxide and hydrogen. A catalyst precursor such as rhodium acetylacetonate dicarbonyl (hereinafter described as "Rh(acac)(CO)$_2$"), Rh$_2$O$_3$, Rh$_4$(CO)$_{12}$, Rh$_6$(CO)$_{16}$ and Rh(NO$_3$)$_3$ may be introduced into a reaction mixture together with the organic phosphorous compound to form a rhodium hydride carbonyl phosphorous complex having catalytic activity in a reaction container. Alternatively, the rhodium hydride carbonyl phosphorous complex may be prepared in advance to be subsequently introduced into a reactor. Preferred specific examples of the present invention include a method in which Rh(acac)(CO)$_2$ is reacted with the organic phosphorous compound in the presence of a solvent and then it is introduced into a reactor together with an excess of the organic phosphorous compound to obtain a rhodium-organic phosphorous complex having catalytic activity.

It was a surprise for the present inventors that a second-step Diels-Alder reaction product having an internal olefin with a relatively high molecular weight as represented by formula (2) was hydroformylated by a slight amount of a rhodium catalyst. The amount of the rhodium compound to be used for the hydroformylation reaction of the present embodiment is preferably 0.1 to 60 μmol, more preferably 0.1 to 30 μmol, even more preferably 0.2 to 20 μmol, and particularly preferably 0.5 to 10 μmol relative to 1 mol of the C$_{13-19}$ monoolefin represented by formula (2) that is the substrate of the hydroformylation reaction. When the amount of the rhodium compound to be used is less than 60 μmol relative to 1 mol of the C$_{13-19}$ monoolefin, the cost of the rhodium catalyst can be reduced without providing equipments for recovery/recycling of rhodium complexes, and therefore economic burden related to equipments for recovery/recycling can be reduced.

Regarding the hydroformylation reaction of the present embodiment, examples of the organic phosphorous compound which forms a catalyst of the hydroformylation reaction together with the rhodium compound include a phosphine represented by general formula P(—R$_1$)(—R$_2$)(—R$_3$) and a phosphite represented by P(—OR$_1$)(—OR$_2$)(—OR$_3$). Specific examples of R$_1$, R$_2$ and R$_3$ include an aryl group, which may be substituted with a C$_{1-4}$ alkyl group or alkoxy group, and an alicyclic alkyl group, which may be substituted with a C$_{1-4}$ alkyl group or alkoxy group, and preferably used are triphenyl phosphine and triphenyl phosphite. The amount of the organic phosphorous compound to be used is preferably 300 to 10000 times, more preferably 500 to 10000 times, even more preferably 700 to 5000 times, and particularly preferably 900 to 2000 times the molar quantity of the rhodium compound. When the amount of the organic phosphorous compound to be used is less than 300 times the molar quantity of the rhodium compound, the stability of the rhodium hydride carbonyl phosphorous complex that is a catalytically active species is impaired, which may result in, for example, slowing of the reaction progress, and therefore it is undesirable. When the amount of the organic phosphorous compound to be used is more than 10000 times the molar quantity of the rhodium metal, the cost related to the organic phosphorous compound increases, and therefore it is undesirable.

The hydroformylation reaction of the present embodiment can be performed without use of a solvent, but can be more suitably performed by use of a reaction-inert solvent. The solvent is not particularly limited as long as it dissolves the C$_{13-19}$ monoolefin represented by formula (2), the rhodium compound and the organic phosphorous compound. Specific examples of the solvent include: hydrocarbons such as aliphatic hydrocarbon, alicyclic hydrocarbon and aromatic hydrocarbon; esters such as aliphatic ester, alicyclic ester and aromatic ester; alcohols such as aliphatic alcohol and alicyclic alcohol; and aromatic halide. Among them, hydrocarbons are preferably used, and among them, alicyclic hydrocarbon and aromatic hydrocarbon are particularly preferably used.

The temperature at the time of performing the hydroformylation reaction of the present embodiment is preferably 40° C. to 160° C., and more preferably 80° C. to 140° C. When the reaction temperature is 40° C. or higher, a sufficient reaction rate is obtained, and remaining of the monoolefin as the raw material can be suppressed. Further, when the reaction temperature is 160° C. or lower, the production of by-products derived from the raw material monoolefin and reaction product can be suppressed to prevent reduction in reaction performance.

When performing the hydroformylation reaction of the present embodiment, it is required to perform the reaction under elevated pressure using carbon monoxide (hereinafter sometimes described as "CO") and hydrogen (hereinafter sometimes described as "H$_2$") gas. CO and H$_2$ gas can be each independently introduced into the reaction system. Alternatively, a mixed gas thereof can be prepared in advance to be introduced into the reaction system. The molar ratio between CO and H$_2$ gas to be introduced into the reaction system (=CO/H$_2$) is preferably 0.2 to 5, more preferably 0.5 to 2, and even more preferably 0.8 to 1.2. When the molar ratio between CO and H$_2$ gas is not within the range, the reaction activity of the hydroformylation reaction and the selectivity of target aldehyde may be reduced. The amount of CO and H$_2$ gas introduced into the reaction system decreases as the reaction proceeds. Therefore, when utilizing a mixed gas of CO and H$_2$ prepared in advance, the reaction may be conveniently controlled.

The reaction pressure of the hydroformylation reaction of the present embodiment is preferably 1 to 12 MPa, more preferably 1.2 to 9 MPa, and even more preferably 1.5 to 5 MPa. When the reaction pressure is 1 MPa or more, a sufficient reaction rate is obtained, and remaining of the monoolefin as the raw material can be suppressed. Further, when the reaction pressure is 12 MPa or less, expensive equipments having excellent pressure resistance are no longer required, and therefore it is economically advantageous. In particular, in the case of performing the reaction by the batch method or semibatch method, it is required to discharge CO and H$_2$ gas to reduce the pressure after the reaction is completed, and the lower the pressure is, the smaller the loss of CO and H$_2$ gas is, and therefore it is economically advantageous.

As the reaction method for performing the hydroformylation reaction of the present embodiment, the batch reaction or the semibatch reaction is preferably employed. The semibatch reaction can be performed by putting the rhodium compound, the organic phosphorous compound and the solvent into a reactor, carrying out pressurization with CO/H$_2$ gas, heating, etc. to obtain the already-described reaction conditions, and then by supplying the monoolefin as the raw material or a solution thereof to the reactor.

The reaction product obtained by the hydroformylation reaction of the present embodiment can be purified by means of distillation, extraction, crystallization or the like.

Another embodiment of the present invention is a method for producing a bifunctional compound represented by formula (3) below, the method having a step of reducing a bifunctional compound represented by formula (1) below in the presence of a catalyst having hydrogenation activity and hydrogen.

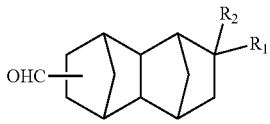
(1)

In the formula: $R_1$ represents $COOCH_3$, $COOC_2H_5$, $COOC_3H_7$, $COOC_4H_9$ or CHO; and $R_2$ represents H, $CH_3$ or $C_2H_5$. $R_1$ is preferably $COOCH_3$ or CHO, and $R_2$ is preferably H or $CH_3$. Further, an embodiment in which $R_1$ represents CHO while $R_2$ represents $C_2H_5$ is also preferred.

(3)

In the formula, $R_2$ represents H, $CH_3$ or $C_2H_5$. $R_2$ is preferably H or $CH_3$.

The bifunctional compound having a norbornane skeleton represented by formula (3) above exhibits excellent characteristics when used as an adhesive or resin raw material.

A $C_{14-16}$ bifunctional compound represented by formula (3) of the present embodiment can be synthesized by a route shown in formula (I) below using, as raw materials, dicyclopentadiene or cyclopentadiene and an olefin having a functional group.

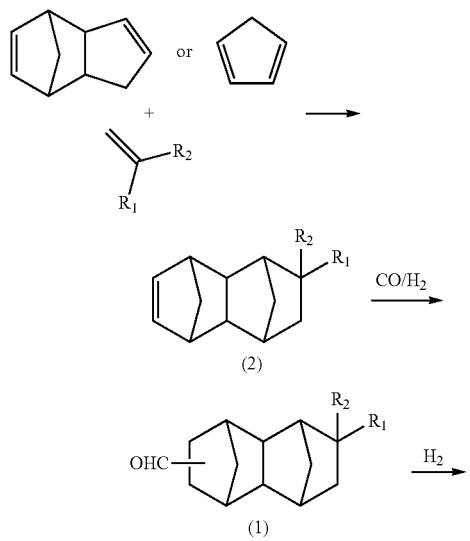
(I)

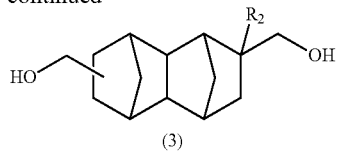
(3)

In the formula: $R_1$ represents $COOCH_3$, $COOC_2H_5$, $COOC_3H_7$, $COOC_4H_9$ or CHO; and $R_2$ represents H, $CH_3$ or $C_2H_5$. $R_1$ is preferably $COOCH_3$ or CHO, and $R_2$ is preferably H or $CH_3$. Further, an embodiment in which $R_1$ represents CHO while $R_2$ represents $C_2H_5$ is also preferred.

[Production of $C_{13-19}$ Monoolefin Represented by Formula (2)]

In the present embodiment, the $C_{13-19}$ monoolefin represented by formula (2) can be produced by performing a Diels-Alder reaction of a monoolefin having a functional group with dicyclopentadiene. Explanations in this regard are the same as those in the paragraphs above.

[Production of $C_{14-20}$ Bifunctional Compound Represented by Formula (1)]

In the present embodiment, a $C_{14-20}$ bifunctional compound represented by formula (1) in formula (I) above can be produced by subjecting a $C_{13-19}$ monoolefin represented by formula (2), carbon monoxide and hydrogen gases to a hydroformylation reaction in the presence of a rhodium compound and an organic phosphorous compound. Explanations in this regard are the same as those in the paragraphs above.

The reaction product obtained by the hydroformylation reaction can be directly used as a raw material for the next reduction reaction, but may also be purified by means of distillation, extraction, crystallization or the like and then used in the next process.

[Production of $C_{14-16}$ Bifunctional Compound Represented by Formula (3)]

In the present embodiment, the $C_{14-16}$ bifunctional compound represented by formula (3) in formula (I) above can be produced by reducing the $C_{14-20}$ bifunctional compound represented by formula (1) in the presence of a catalyst having hydrogenation activity and hydrogen.

In the reduction reaction of the present embodiment, as the catalyst having hydrogenation activity, a catalyst comprising at least one element selected from the group consisting of copper, chromium, iron, zinc, aluminium, nickel, cobalt and palladium is used. Examples of the catalyst include a Cu—Cr catalyst, a Cu—Zn catalyst, a Cu—Zn—Al catalyst, a Raney-Ni catalyst and a Raney-Co catalyst.

The amount of the aforementioned hydrogenation catalyst to be used is 1 to 100% by weight, preferably 2 to 50% by weight, and more preferably 5 to 30% by weight relative to the $C_{14-20}$ bifunctional compound represented by formula (1) as the substrate. When the amount of the catalyst to be used is within the range, the hydrogenation reaction can be suitably performed. When the amount of the catalyst to be used is small, the reaction is not completed, and as a result, the yield of the objective substance is reduced. Further, when the amount of the catalyst to be used is large, it is impossible to obtain the effect of improving the reaction rate commensurate with the amount of the catalyst used in the reaction.

The reaction temperature for the reduction reaction of the present embodiment is preferably 80 to 250° C., and more preferably 100 to 230° C. When the reaction temperature is 250° C. or lower, occurrence of side reaction and decomposition reaction can be suppressed and the objective substance can be obtained in a high yield. When the reaction temperature is 80° C. or higher, the reaction can be completed within an appropriate amount of time, and reduction in productivity and reduction in the yield of the objective substance can be avoided.

Regarding the reaction pressure of the reduction reaction of the present embodiment, the hydrogen partial pressure is preferably 1 to 20 MPa, and more preferably 2 to 15 MPa. When the hydrogen partial pressure is 20 MPa or less, occurrence of side reaction and decomposition reaction can be suppressed and the objective substance can be obtained in a high yield. When the hydrogen partial pressure is 1 MPa or more, the reaction can be completed within an appropriate amount of time, and reduction in productivity and reduction in the yield of the objective substance can be avoided. Note that a gas which is inactive in the reduction reaction (for example, nitrogen or argon) can coexist.

In the reduction reaction of the present embodiment, a solvent can be used. As the solvent, aliphatic hydrocarbons, alicyclic hydrocarbons, aromatic hydrocarbons, alcohols, etc. can be used, and among them, preferred are alicyclic hydrocarbons, aromatic hydrocarbons and alcohols. Specific examples thereof include cyclohexane, toluene, xylene, methanol, ethanol, 1-propanol and cyclohexanol.

As the reaction method of the reduction reaction of the present embodiment, various reaction methods can be employed, and examples thereof include: the batch method using a tank reactor or the like; the semibatch method in which a substrate or substrate solution is supplied to a tank reactor under reaction conditions; and the continuous flow method in which a substrate or substrate solution is flowed through a tube reactor filled with a molded catalyst under reaction conditions.

The reaction product obtained by the reduction reaction of the present embodiment can be purified by means of distillation, extraction, crystallization or the like.

Yet another embodiment of the present invention is an isomer mixture of: a 2,6-derivative of a bifunctional compound represented by formula (3-a) below; and a 2,7-derivative of a bifunctional compound represented by formula (3-b) below, wherein the mixing ratio between the 2,6-derivative and the 2,7-derivative is 20:80 to 80:20.

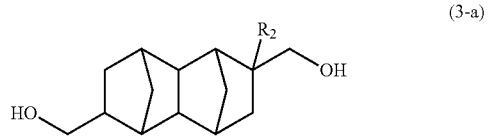

(In the formula, $R_2$ represents H, $CH_3$ or $C_2H_5$.)

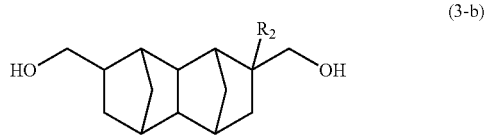

(In the formula, $R_2$ represents H, $CH_3$ or $C_2H_5$.)

The isomer mixture of the 2,6-derivative of the bifunctional compound represented by formula (3-a) and the 2,7-derivative of the bifunctional compound represented by formula (3-b) can be produced according to the method for producing the $C_{14-16}$ bifunctional compound represented by formula (3).

In the isomer mixture of the present invention, the mixing ratio between the 2,6-derivative and the 2,7-derivative is 20:80 to 80:20, preferably 25:75 to 75:25, and more preferably 30:70 to 70:30. When the mixing ratio of the 2,6-derivative is smaller than 20:80, characteristics as a paint additive, adhesive, resin raw material or the like may be impaired. When the mixing ratio of the 2,6-derivative is larger than 80:20, characteristics as a paint additive, adhesive, resin raw material or the like may also be impaired.

The mixing ratio between the 2,6-derivative and the 2,7-derivative can be adjusted by purifying an aldehyde ester derivative as the intermediate product or a diol derivative as the final product by distillation. In the aldehyde ester derivative, a monoester derivative (polymerization inhibitor) is included, and at the time of removing this by purification by distillation, the 2,7-derivative is removed together. It is considered that for this reason, the ratio of the 2,6-derivative in the product isolated by distillation is increased. Further, the ratio of the 2,6-derivative can also be increased by purifying the diol derivative by distillation.

The isomer mixture of the present invention is particularly preferably used as a row material for a polycarbonate resin, and the polycarbonate resin obtained has excellent effects in terms of a refractive index, Abbe number and elongation rate at yield.

EXAMPLES

Hereinafter, the present invention will be specifically described by way of working examples, but the present invention is not limited to the working examples.

<Analysis Method>
1) Gas Chromatography Measurement Conditions
    Analyzer: Capillary Gas Chromatograph GC-2010 Plus manufactured by Shimadzu Corporation
    Analysis column: InertCap 1 manufactured by GL Sciences Inc. (30 m, 0.32 mm I.D., film thickness: 0.25 μm)
    Temperature of oven: 60° C. (0.5 minute)-15° C./min-280° C. (4 minutes)
    Detector: FID, temperature: 280° C.
2) GC-MS Measurement Conditions
    Analyzer: GCMS-QP2010 Plus manufactured by Shimadzu Corporation
    Ionization voltage: 70 eV
    Analysis column: DB-1 manufactured by Agilent Technologies (30 m, 0.32 mm I.D., film thickness: 1.00 μm)
    Temperature of oven: 60° C. (0.5 minute)-15° C./min-280° C. (4 minutes) Temperature of detector Example 1A 156 g (1.81 mol) of methyl acrylate and 150 g (1.14 mol) of dicyclopentadiene were put into a 500 ml stainless steel reactor, and the mixture was reacted at 195° C. for 2 hours. A reaction solution containing 87 g of a monoolefin represented by formula (2b) below (methyl-1,2,3,4,4a,5,8,8a-octahydro-1,4:5,8-dimethanonaphthalene-2-carboxylate) was obtained, and this was purified by distillation, and after that, a part of the product was used in the following reaction.

With a 300 ml stainless steel reactor, the hydroformylation reaction of the monoolefin represented by formula (2b) was performed using a $CO/H_2$ mixed gas (molar ratio of $CO/H_2=1$). 70 g of the monoolefin represented by formula (2b), 140 g of toluene, 0.50 g of triphenyl phosphite and 550 µl of a separately prepared toluene solution of Rh(acae) (CO)$_2$ (concentration: 0.003 mol/L) were put into the reactor. Substitution with nitrogen and substitution with the CO/H$_2$ mixed gas were performed 3 times each. After that, the inside of the system was pressurized with the CO/H$_2$ mixed gas, and the reaction was performed at 100° C. and 2 MPa for 5 hours.

After the reaction was completed, gas chromatography analysis and GC-MS analysis of the reaction solution were carried out under the above-described conditions to confirm that the reaction solution contains 76 g of the main product having a molecular weight of 248 and 1.4 g of the monoolefin represented by formula (2b) (conversion rate: 98%, selectivity of the main product: 97%).

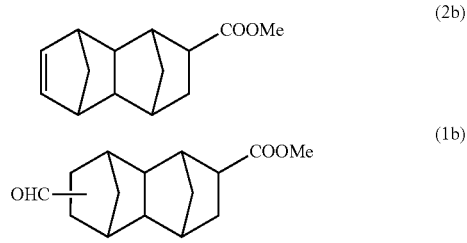

(In the formula, Me represents a methyl group.)

Next, a part of the reaction solution obtained by the hydroformylation reaction was distilled using a spinning band distillation apparatus to obtain a fraction having a boiling point of 154 to 159° C. (1 to 1.5 Torr.).

<Identification of Product>

NMR analysis of the component obtained in Example 1A was carried out. NMR spectra are shown in FIGS. 1 to 3.

(NMR Measurement Conditions)

Apparatus: JNM-ECA500 (500 MHz) manufactured by JEOL Ltd.
Measurement mode: 1H-NMR, 13C-NMR, COSY-NMR
Solvent: CDCl$_3$ (deuterochloroform)
Internal standard substance: tetramethylsilane According to the results of GC-MS analysis and NMR analysis shown in FIGS. 1 to 3, it was confirmed that the main product obtained in Example 1A is the bifunctional compound represented by formula (1b). Further, it was found that the obtained product isolated by distillation is an isomer mixture containing the 2,6-derivative (73%) and the 2,7-derivative (27%) (based on the weight ratio).

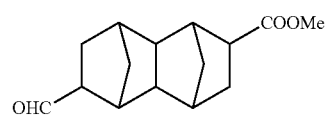 [SMILES: COC(=O)C1CC2CC1C1C3CC(C=O)C(C3)C21]

Methyl 6-formyldecahydro-1,4:5,8-dimethanonaphthalene-2-carboxylate

Methyl 7-formyldecahydro-1,4:5,8-dimethanonaphthalene-2-carboxylate

Example 2A

The reaction was performed using 181 g (1.81 mol) of methyl methacrylate instead of methyl acrylate of Example 1A to obtain a reaction solution containing 91 g of a monoolefin represented by formula (2a) below. This was purified by distillation, and after that, a part of the product was used in the following reaction.

With a 300 ml stainless steel reactor, the hydroformylation reaction of the monoolefin represented by formula (2a) was performed using a CO/H$_2$ mixed gas (molar ratio of CO/H$_2$=1). 70 g of the monoolefin represented by formula (2a), 140 g of toluene, 0.47 g of triphenyl phosphite and 500 µl of a separately prepared toluene solution of Rh(acac) (CO)$_2$ (concentration: 0.003 mol/L) were put into the reactor. Substitution with nitrogen and substitution with the CO/H$_2$ mixed gas were performed 3 times each. After that, the inside of the system was pressurized with the CO/H$_2$ mixed gas, and the reaction was performed at 100° C. and 2 MPa for 5 hours. After the reaction was completed, gas chromatography analysis and GC-MS analysis of the reaction solution were carried out under the above-described conditions. According to the results of Example 1A, it was inferred that a bifunctional compound represented by formula (1a) below is the main product. According to GC-MS analysis, it was confirmed that the molecular weight of the main product is the same as that of formula (1a). According to the subsequent analysis, it was confirmed that 75 g of the compound of formula (1a) and 2.2 g of the monoolefin represented by formula (2a) are contained in the reaction solution after the reaction (conversion rate: 97%, selectivity: 98%). Further, it was confirmed that formula (1a) is an isomer mixture containing the 2,6-derivative (50%) and the 2,7-derivative (50%) (based on the weight ratio).

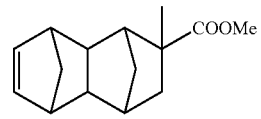

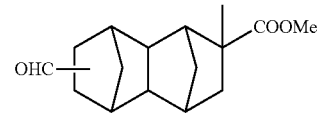

(In the formula, Me represents a methyl group.)

Example 3A 63 g of a monoolefin represented by formula (2c) below was synthesized using 127 g (1.74 mol/purity: 96%) of methacrolein instead of methyl acrylate of Example 1A. The reaction was performed twice, and after purification by distillation, a part of the product was used in the following reaction.

With a 300 ml stainless steel reactor, the hydroformylation reaction of the monoolefin represented by formula (2c) was performed using a CO/H$_2$ mixed gas (molar ratio of CO/H$_2$=1). 70 g of the monoolefin represented by formula (2c), 140 g of toluene, 0.55 g of triphenyl phosphite and 580 µl of a separately prepared toluene solution of Rh(acac)

(CO)₂ (concentration: 0.003 mol/L) were put into the reactor. Substitution with nitrogen and substitution with the CO/H₂ mixed gas were performed 3 times each. After that, the inside of the system was pressurized with the CO/H₂ mixed gas, and the reaction was performed at 100° C. and 2 MPa for 6 hours. After the reaction was completed, gas chromatography analysis and GC-MS analysis of the reaction solution were carried out under the above-described conditions to confirm that the reaction solution contains 77 g of the main product having a molecular weight of 232 and 1.3 g of the monoolefin represented by formula (2c) (conversion rate: 98%, selectivity: 98%).

According to GC-MS analysis and the product of Example 1A, it was inferred that the obtained main product is a bifunctional compound represented by formula (1c) below.

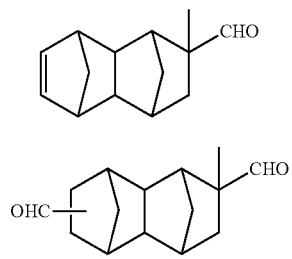

Example 4A

With a 300 ml stainless steel reactor, the hydroformylation reaction of the monoolefin represented by formula (2a) below was performed using a CO/H₂ mixed gas (molar ratio of CO/H₂=1). 70 g of the monoolefin represented by formula (2a), 140 g of toluene, 0.39 g of triphenyl phosphine and 500 µl of a separately prepared toluene solution of Rh(acac)(CO)₂ (concentration: 0.003 mol/L) were put into the reactor. Substitution with nitrogen and substitution with the CO/H₂ mixed gas were performed 3 times each. After that, the inside of the system was pressurized with the CO/H₂ mixed gas, and the reaction was performed at 100° C. and 2 MPa for 5 hours.

After the reaction was completed, gas chromatography analysis of the reaction solution was carried out under the above-described conditions. As a result, it was confirmed that it is a reaction solution containing 74 g of the bifunctional compound represented by formula (1a) and 2.8 g of the monoolefin represented by formula (2a) below (conversion rate: 96%, selectivity: 98%). Further, it was found that the obtained reaction solution is an isomer mixture containing the 2,6-derivative (50%) and the 2,7-derivative (50%) (based on the weight ratio).

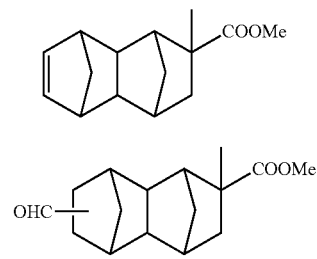

(In the formula, Me represents a methyl group.)

Example 5A

With a 300 ml stainless steel reactor, the hydroformylation reaction of the monoolefin represented by formula (2b) below was performed using a CO/H₂ mixed gas (molar ratio of CO/H₂=1). 70 g of the monoolefin represented by formula (2b) and 100 g of toluene were put into a stainless steel tank, and substitution with nitrogen and substitution with the CO/H₂ mixed gas were performed 3 times each. After that, the inside of the system was slightly pressurized with the CO/H₂ mixed gas. Separately, 40 g of toluene, 0.13 g of triphenyl phosphite and 120 µl of a separately prepared toluene solution of Rh(acac)(CO)₂ (concentration: 0.003 mol/L) were put into the 300 ml stainless steel reactor. Substitution with nitrogen and substitution with the CO/H₂ mixed gas were performed 3 times each. After that, the inside of the system was pressurized with the CO/H₂ mixed gas and held at 100° C. and 2 MPa. From the stainless steel tank, the toluene solution of the monoolefin represented by formula (2b) was supplied to the reactor over 2 hours (during this, the reactor was controlled at 100° C. and 2 MPa). After the supply was completed, the mixture was maintained at 100° C. and 2 MPa for 3 hours.

After the reaction was completed, gas chromatography analysis of the reaction solution was carried out under the above-described conditions. As a result, it was confirmed that it is a reaction solution containing 78 g of the bifunctional compound represented by formula (1b) below and 0.73 g of the monoolefin represented by formula (2b) below (conversion rate: 99%, selectivity: 99%). Further, it was found that the obtained reaction solution is an isomer mixture containing the 2,6-derivative (50%) and the 2,7-derivative (50%) (based on the weight ratio).

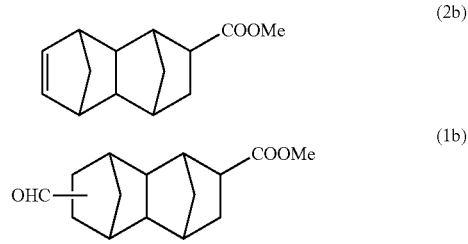

(In the formula, Me represents a methyl group.)

Example 6A

A reaction solution containing 14 g of a monoolefin represented by formula (2d) below was obtained using 52 g (0.61 mol/purity: 99%) of ethylacrolein instead of methyl acrylate of Example 1A. The reaction was performed twice, and after purification by distillation, a part of the product was used in the following reaction.

With a 300 ml stainless steel reactor, the hydroformylation reaction of the monoolefin represented by formula (2d) was performed using a CO/H₂ mixed gas (molar ratio of CO/H₂=1). 21.3 g of the monoolefin represented by formula (2d), 20 g of toluene, 518 mg of triphenyl phosphine and 128 d of a separately prepared toluene solution of Rh(acac)(CO)₂ (concentration: 0.0384 mol/L) were put into the reactor. Substitution with nitrogen and substitution with the CO/H₂ mixed gas were performed 3 times each. After that, the inside of the system was pressurized with the CO/H$_2$ mixed gas, and the reaction was performed at 110° C. and 2 MPa for 1.5 hours. After the reaction was completed, gas chromatography analysis of the reaction solution was carried out under the above-described conditions. As a result, it was confirmed that it is a reaction solution containing 23.8 g of the bifunctional compound represented by formula (1d) below (yield: 98%).

According to GC-MS analysis and the product of Example 1A, it was inferred that the obtained main product is a bifunctional compound represented by formula (1d) below.

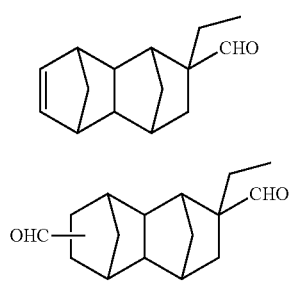

Example 1B 173 g (2.01 mol) of methyl acrylate and 167 g (1.26 mol) of dicyclopentadiene were put into a 500 ml stainless steel reactor, and the mixture was reacted at 195° C. for 2 hours. A reaction solution containing 96 g of the monoolefin represented by formula (2b) below was obtained. This was purified by distillation, and then a part of the product was used in the following reaction.

With a 300 ml stainless steel reactor, the hydroformylation reaction of the monoolefin represented by formula (2b) purified by distillation was performed using a CO/H$_2$ mixed gas (molar ratio of CO/H$_2$=1). 70 g of the monoolefin represented by formula (2b), 140 g of toluene, 0.50 g of triphenyl phosphite and 550 μl of a separately prepared toluene solution of Rh(acac)(CO)$_2$ (concentration: 0.003 mol/L) were put into the reactor. Substitution with nitrogen and substitution with the CO/H$_2$ mixed gas were performed 3 times each. After that, the inside of the system was pressurized with the CO/H$_2$ mixed gas, and the reaction was performed at 100° C. and 2 MPa for 5 hours. After the reaction was completed, gas chromatography analysis of the reaction solution was carried out under the above-described conditions to confirm that the reaction solution contains 76 g of the bifunctional compound represented by formula (1b) below and 1.4 g of the monoolefin represented by formula (2b) (conversion rate: 98%, selectivity: 97%). This was purified by distillation, and then a part of the product was used in the following reaction.

50 g of the bifunctional compound represented by formula (1b) purified by distillation, 10 g of a Cu—Zn—Al catalyst (E-01X manufactured by JGC Catalysts and Chemicals Ltd.) and 150 g of toluene were put into a 300 ml stainless steel reactor. The inside of the system was pressurized with hydrogen gas, and the reaction was performed at 10 MPa and 215° C. for 8 hours. After the reaction, the obtained slurry was diluted with methanol and the catalyst was filtered off using a membrane filter having a pore diameter of 0.2 μm. After that, the solvent was distilled off using an evaporator, and gas chromatography analysis and GC-MS analysis were carried out under the above-described conditions to confirm that 43 g of the main product having a molecular weight of 222 was contained (yield of the main product: 96%). This was further purified by distillation to obtain the main product.

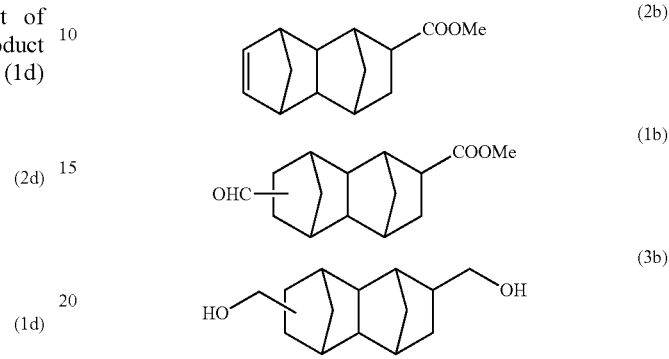

(In the formula, Me represents a methyl group.)

<Identification of Product>

NMR analysis of the component obtained in Example 1B was carried out. NMR spectra are shown in FIGS. 4 to 6.

(NMR Measurement Conditions)
Apparatus: JNM-ECA500 (500 MHz) manufactured by JEOL Ltd.
Measurement mode: 1H-NMR, 13C-NMR, COSY-NMR
Solvent: CD$_3$OD (deuterated methanol)
Internal standard substance: tetramethylsilane According to the results of GC-MS analysis and NMR analysis shown in FIGS. 4 to 6, it was confirmed that the main product obtained in Example 1B is the bifunctional compound represented by formula (3b). Further, it was found that the obtained product isolated by distillation is an isomer mixture containing the 2,6-derivative (76%) and the 2,7-derivative (24%) (based on the weight ratio).

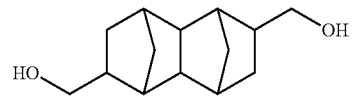 [SMILES: OCC1CC2CC1C1C3CC(CO)C(C3)C21]

(Decahydro-1,4:5,8-dimethanonaphthalene-2,6-diyl) dimethanol

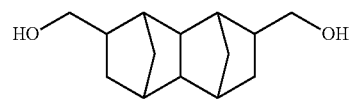

(Decahydro-1,4:5,8-dimethanonaphthalene-2,7-diyl) dimethanol

Example 2B

A reaction solution containing 86 g of a monoolefin represented by formula (2c) below was obtained using 141 g (1.93 mol/purity: 96%) of methacrolein instead of methyl acrylate of Example 1B. This was purified by distillation, and after that, a part of the product was used in the following reaction.

With a 300 ml stainless steel reactor, the hydroformylation reaction of the monoolefin represented by formula (2c) was performed using a CO/H$_2$ mixed gas (molar ratio of CO/H$_2$=1). 70 g of the monoolefin represented by formula (2c), 140 g of toluene, 0.55 g of triphenyl phosphite and 580 μl of a separately prepared toluene solution of Rh(acac)(CO)$_2$ (concentration: 0.003 mol/L) were put into the reactor. Substitution with nitrogen and substitution with the CO/H$_2$ mixed gas were performed 3 times each. After that, the inside of the system was pressurized with the CO/H$_2$ mixed gas, and the reaction was performed at 100° C. and 2 MPa for 6 hours. After the reaction was completed, gas chromatography analysis of the reaction solution was carried out under the above-described conditions. As a result, it was confirmed that it is a reaction solution containing 77 g of the bifunctional compound represented by formula (1c) below and 1.3 g of the monoolefin represented by formula (2c) below (conversion rate: 98%, selectivity: 98%).

50 g of the bifunctional compound represented by formula (1c) purified by distillation, 150 g of toluene and 10 ml of a Raney cobalt catalyst were put into a 300 ml stainless steel reactor. The inside of the system was pressurized with hydrogen gas, and the reaction was performed at 4 MPa and 100° C. for 5 hours. After the reaction, the obtained slurry was diluted with methanol and the catalyst was filtered off using a membrane filter having a pore diameter of 0.2 μm. The solvent was distilled off using an evaporator, and gas chromatography analysis and GC-MS analysis were carried out under the above-described conditions. Based on the results of Example 1B, it was inferred that the main product is a bifunctional compound represented by formula (3c) below. According to GC-MS analysis, it was confirmed that the molecular weight of the main product is the same as that of formula (3c). Further, it was also confirmed that the amount of the bifunctional compound represented by formula (3c) produced is 49 g (yield: 96%).

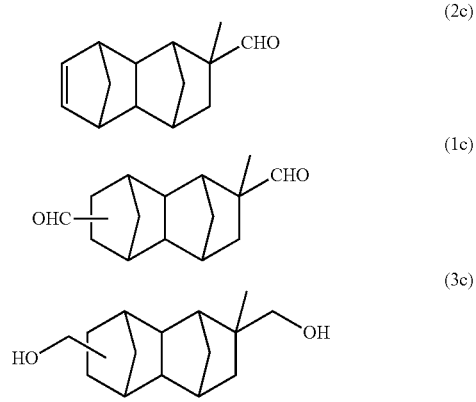

Example 3B

The monoolefin represented by formula (2b) above was synthesized and purified by distillation in a manner similar to that in Example 1B.

With a 300 ml stainless steel reactor, the hydroformylation reaction of the monoolefin represented by formula (2b) was performed using a CO/H$_2$ mixed gas (molar ratio of CO/H$_2$=1). 70 g of the monoolefin represented by formula (2b) and 100 g of toluene were put into a stainless steel tank, and substitution with nitrogen and substitution with the CO/H$_2$ mixed gas were performed 3 times each. After that, the inside of the system was slightly pressurized with the CO/H$_2$ mixed gas. Separately, 40 g of toluene, 0.13 g of triphenyl phosphite and 120 μl of a separately prepared toluene solution of Rh(acac)(CO)$_2$ (concentration: 0.003 mol/L) were put into the 300 ml stainless steel reactor. Substitution with nitrogen and substitution with the CO/H$_2$ mixed gas were performed 3 times each. After that, the inside of the system was pressurized with the CO/H$_2$ mixed gas and held at 100° C. and 2 MPa. From the stainless steel tank, the toluene solution of the monoolefin represented by formula (2b) was supplied to the reactor over 2 hours (during this, the reactor was controlled at 100° C. and 2 MPa). After the supply was completed, the mixture was maintained at 100° C. and 2 MPa for 3 hours. After the reaction was completed, gas chromatography analysis of the reaction solution was carried out under the above-described conditions. As a result, it was confirmed that it is a reaction solution containing 78 g of the bifunctional compound represented by formula (1b) above and 0.73 g of the monoolefin represented by formula (2b) above (conversion rate: 99%, selectivity: 99%).

In a manner similar to that in Example 1B, the reduction reaction was performed using the bifunctional compound represented by formula (1b) as the raw material (reaction yield: 96%), and the obtained product was further subjected to purification by distillation, thereby obtaining the bifunctional compound represented by formula (3b) above. It was found that the obtained product isolated by distillation is an isomer mixture containing the 2,6-derivative (52%) and the 2,7-derivative (48%) (based on the weight ratio).

Example 4B

A reaction solution containing 14 g of a monoolefin represented by formula (2d) below was obtained using 52 g (0.61 mol/purity: 99%) of ethylacrolein instead of methyl acrylate of Example 1B. The reaction was performed twice, and after purification by distillation, a part of the product was used in the following reaction.

With a 300 ml stainless steel reactor, the hydroformylation reaction of the monoolefin represented by formula (2d) was performed using a CO/H$_2$ mixed gas (molar ratio of CO/H$_2$=1). 21.3 g of the monoolefin represented by formula (2d), 20 g of toluene, 518 mg of triphenyl phosphine and 128 μl of a separately prepared toluene solution of Rh(acac)(CO)$_2$ (concentration: 0.0384 mol/L) were put into the reactor. Substitution with nitrogen and substitution with the CO/H$_2$ mixed gas were performed 3 times each. After that, the inside of the system was pressurized with the CO/H$_2$ mixed gas, and the reaction was performed at 110° C. and 2 MPa for 1.5 hours. After the reaction was completed, gas chromatography analysis of the reaction solution was carried out under the above-described conditions. As a result, it was confirmed that it is a reaction solution containing 23.8 g of the bifunctional compound represented by formula (1d) below (yield: 98%).

The reaction solution containing 22.7 g of the bifunctional compound represented by formula (1d), 38 g of cyclohexanol and 2.2 g of a Cu—Zn—Al catalyst (E-01X manufactured by JGC Catalysts and Chemicals Ltd.) were put into a 300 ml stainless steel reactor. The inside of the system was pressurized with hydrogen gas, and the reaction was performed at 3 MPa and 140° C. for 1.5 hours. After the reaction, the obtained slurry was diluted with methanol and the catalyst was filtered off using a membrane filter having a pore diameter of 0.2 μm. The solvent was distilled off using an evaporator, and gas chromatography analysis and GC-MS analysis were carried out under the above-described conditions. Based on the results of Example 1B, it was inferred that the main product is a bifunctional compound represented by formula (3d) below. According to GC-MS analysis, it was confirmed that the molecular weight of the main product is the same as that of formula (3d). Further, it was also confirmed that the amount of the bifunctional compound represented by formula (3d) produced is 22 g (yield: 96%).

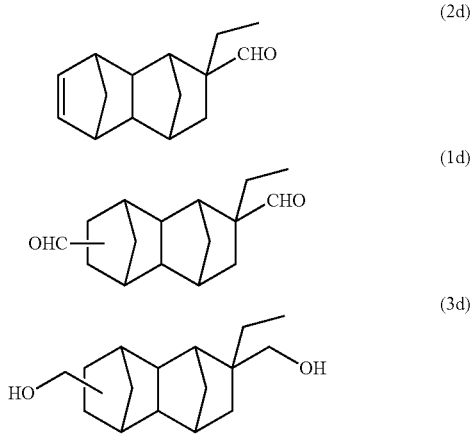

In order to show utility of the isomer mixture of the 2,6-derivative and the 2,7-derivative of the bifunctional compound of the present invention, a polycarbonate resin was produced using the isomer mixture and evaluation thereof was carried out, as described in Reference Example 1 below.
<Method for Evaluation of Polycarbonate Resin>
1) Refractive Index, Abbe Number The polycarbonate resin was press-molded into a circular plate (40φ, thickness: 3 mm) (molding conditions: 200° C., 100 kgf/cm$^2$, 2 minutes). It was cut at right angles to be measured with Kalnew KPR-200.
2) Elongation Rate at Yield Based on JIS K7113, the polycarbonate resin was molded into the shape of type-1 test piece, and it was measured (tensile speed: 2 min/min).

Reference Example 1

30.9 g (0.139 mol) of the bifunctional compound represented by formula (3b) obtained in Example 1B (isomer mixture in which the isomer with a hydroxymethyl group at 2,6-position=76% and the isomer with a hydroxymethyl group at 2,7-position=24%), 29.8 g (0.139 mol) of diphenyl carbonate and 0.09 mg (1.1 μmol) of sodium hydrogencarbonate were put into a 300 mL reactor equipped with a stirrer and a distillation apparatus and it was heated in oil bath under nitrogen atmosphere (760 Torr), and a transesterification reaction was initiated when the temperature reached 200° C.

5 minutes after the initiation of the reaction, stirring was started, and 20 minutes later, the pressure was reduced from 760 Torr to 200 Torr over 10 minutes. The temperature was increased to 210° C. while reducing the pressure, and increased to reach 220° C. at 70 minutes after the initiation of the reaction. 80 minutes after the initiation of the reaction, the pressure was reduced to 150 Torr over 30 minutes, and the temperature was increased to 240° C. while reducing the pressure to 1 Torr. After that, it was kept for 10 minutes, thereby obtaining a polycarbonate resin.

The refractive index of the obtained polycarbonate resin was 1.531, and the Abbe number was 57.3. Further, the elongation rate at yield of the obtained polycarbonate resin was 150%.

Reference Example 2

The bifunctional compound represented by formula (3b) obtained in Example 1B (isomer mixture in which the isomer with a hydroxymethyl group at 2,6-position=76% and the isomer with a hydroxymethyl group at 2,7-position=24%) was subjected to distillation to obtain a bifunctional compound having a hydroxymethyl group at 2,6-position (isomer purity: 99.5%). This was used as a raw material to synthesize a polycarbonate resin under conditions similar to those in Reference Example 1.

Using the obtained polycarbonate resin, a disk-like molding for the measurement of optical characteristics was molded. In the molding, there was white turbidity caused by crystallization, and it was not enough for evaluating the refractive index and Abbe number as an optical material. Further, the elongation rate at yield of the obtained polycarbonate resin was 50%.

Reference Example 3

The bifunctional compound comprising the 2,6-derivetive (=52%) and the 2,7-derivetive (=48%) obtained in Example 3B was used as a raw material to synthesize a polycarbonate resin under conditions similar to those in Reference Example 1.

The refractive index of the obtained polycarbonate resin was 1.532, and the Abbe number was 57.2. Further, the elongation rate at yield of the obtained polycarbonate resin was 160%.

Reference Example 4

Methyl acrylate and dicyclopentadiene were used and the process was carried out to the reduction reaction under conditions similar to those in Example 3B, thereby obtaining a bifunctional compound represented by formula (3b) above. Further, it was subjected to purification by distillation to obtain a bifunctional compound represented by formula (3b) above comprising the 2,6-derivetive (=22%) and the 2,7-derivetive (=78%). This was used as a raw material to synthesize a polycarbonate resin under conditions similar to those in Reference Example 1.

The refractive index of the obtained polycarbonate resin was 1.531, and the Abbe number was 57.0. Further, the elongation rate at yield of the obtained polycarbonate resin was 130%.

INDUSTRIAL APPLICABILITY

According to the present invention, it is possible to obtain a novel bifunctional compound having a norbornane skeleton in the molecule and having a skeleton different from those of tricyclodecane dicarbaldehyde and pentacyclopentadecane dicarbaldehyde by means of a method excellent in economic efficiency in industrial practice.

The invention claimed is:

1. A method for producing a bifunctional compound of formula (1):

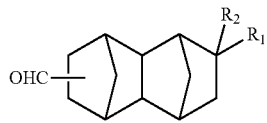

(1)

wherein $R_1$ represents $COOCH_3$, $COOC_2H_5$, $COOC_3H_7$, $COOC_4H_9$ or CHO; and $R_2$ represents H, $CH_3$ or $C_2H_5$, provided that when $R_1$ represents CHO, $R_2$ represents $C_2H_5$, the method comprising subjecting a monoolefin of formula (2):

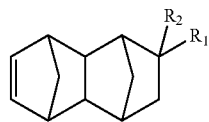

(2)

wherein $R_1$ represents $COOCH_3$, $COOC_2H_5$, $COOC_3H_7$, $COOC_4H_9$ or CHO; and $R_2$ represents H, $CH_3$ or $C_2H_5$, provided that when $R_1$ represents CHO, $R_2$ represents $C_2H_5$, carbon monoxide and hydrogen gases to a hydroformylation reaction in the presence of a rhodium compound and an organic phosphorous compound.

2. The method according to claim 1, further comprising producing the monoolefin of formula (2) by a Diels-Alder reaction of dicyclopentadiene with $CH_2=CR_1R_2$, wherein $R_1$ represents $COOCH_3$, $COOC_2H_5$, $COOC_3H_7$, $COOC_4H_9$ or CHO; and $R_2$ represents H, $CH_3$ or $C_2H_5$, provided that when $R_1$ represents CHO, $R_2$ represents $C_2H_5$.

3. The method according to claim 1, comprising performing the hydroformylation reaction using: the rhodium compound in an amount of 0.1 to 60 μmol relative to 1 mol of the monoolefin of formula (2); and the organic phosphorous compound in an amount of 300 to 10,000 times the molar quantity of the rhodium compound.

4. The method according to claim 1, wherein a pressure at the time of hydroformylation of the monoolefin of formula (2) is 1 to 12 MPa.

5. The method according to claim 1, comprising supplying the monoolefin of formula (2) or a solution thereof to a solution comprising the rhodium compound, the organic phosphorous compound and a solvent under an atmosphere comprising carbon monoxide and hydrogen gases.

6. The method according to claim 1, further comprising isolating the bifunctional compound of formula (1) from a reaction solution after the hydroformylation reaction by distillation.

7. The method according to claim 1, wherein $R_1$ in formula (1) and formula (2) represents $COOCH_3$.

8. The method according to claim 1, wherein $R_1$ in formula (1) and formula (2) represents $COOC_2H_5$.

9. The method according to claim 1, wherein $R_1$ in formula (1) and formula (2) represents $COOC_3H_7$.

10. The method according to claim 1, wherein $R_1$ in formula (1) and formula (2) represents $COOC_4H_9$.

11. The method according to claim 1, wherein $R_1$ in formula (1) and formula (2) represents CHO.

* * * * *